US00PP29667P2

(12) United States Plant Patent
Sakazaki

(10) Patent No.: US PP29,667 P2
(45) Date of Patent: Sep. 11, 2018

(54) ***CALIBRACHOA* PLANT NAMED 'USCAL69404'**

(50) Latin Name: ***Calibrachoa* sp.**
Varietal Denomination: USCAL69404

(71) Applicant: Ushio Sakazaki, Shiga (JP)

(72) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 15/731,453

(22) Filed: Jun. 12, 2017

(51) Int. Cl.
*A01H 5/02* (2018.01)

(52) U.S. Cl.
USPC ..... Plt./413
CPC ..... *A01H 5/02* (2013.01)

(58) Field of Classification Search
USPC ..... Plt./413
CPC ..... A01H 5/02
See application file for complete search history.

(56) References Cited

PUBLICATIONS

GTITM Citation for 'USCAL69404' as per CA PBR 17-9128; Apr. 28, 2017; 1 page.*

* cited by examiner

*Primary Examiner* — Kent L Bell
(74) *Attorney, Agent, or Firm* — C. A. Whealy

(57) ABSTRACT

A new and distinct *Calibrachoa* plant named 'USCAL69404', characterized by its upright to outwardly spreading and mounding to eventually trailing plant habit; moderately vigorous to vigorous growth habit; freely branching habit; dense and bushy appearance; freely flowering habit; scarlet red-colored petals with radiating yellow-colored stripes that extend to the edge of the petal; and good garden performance.

1 Drawing Sheet

Botanical designation: *Calibrachoa* sp.
Cultivar denomination: 'USCAL69404'.

BACKGROUND OF THE INVENTION

The present invention relates to a new and distinct cultivar of *Calibrachoa* plant, botanically known as *Calibrachoa* sp. and hereinafter referred to by the name 'USCAL69404'.

The new *Calibrachoa* plant is a product of a planned breeding program conducted by the Inventor in Higashiomi, Shiga, Japan. The objective of the breeding program is to create new uniform and freely-branching *Calibrachoa* plants with unique and attractive flower coloration and good garden performance.

The new *Calibrachoa* plant originated from a cross-pollination conducted by the Inventor in Higashiomi, Shiga, Japan on May 8, 2014 of a proprietary seedling selection of *Calibrachoa* sp. identified as code number 14CJ21-01, not patented, as the female, or seed, parent with a proprietary selection of *Calibrachoa* sp. identified as code number 14CJ26-02, not patented, as the male, or pollen, parent. The new *Calibrachoa* plant was discovered and first selected by the Inventor as a single flowering plant within the progeny of the stated cross-pollination in a controlled greenhouse environment in Bonsall, Calif. on Jun. 9, 2015.

Asexual reproduction of the new *Calibrachoa* plant by vegetative terminal cuttings in a controlled greenhouse environment in Bonsall, Calif. since Jun. 10, 2015 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'USCAL69404'. These characteristics in combination distinguish 'USCAL69404' as a new and distinct *Calibrachoa* plant:

1. Upright to outwardly spreading and mounding to eventually trailing plant habit.
2. Moderately vigorous to vigorous growth habit.
3. Freely branching habit; dense and bushy appearance.
4. Freely flowering habit.
5. Scarlet red-colored petals with radiating yellow-colored stripes that extend to the edge of the petal.
6. Good garden performance.

The new *Calibrachoa* plant can be compared to plants of the female parent selection. Plants of the new *Calibrachoa* differ primarily from plants of the female parent selection in flower color as plants of the female parent selection have cherry pink-colored petals with creamy yellow-colored stripes.

The new *Calibrachoa* plant can be compared to plants of the male parent selection. Plants of the new *Calibrachoa* differ primarily from plants of the male parent selection in flower color as plants of the male parent selection have cherry red-colored petals with yellow-colored stripes that extend halfway to the edge of the petal.

Plants of the new *Calibrachoa* can be compared to plants of the *Calibrachoa* sp. 'USCAL91001', disclosed in U.S. Plant Pat. No. 23,232. In side-by-side comparisons, plants of the new *Calibrachoa* differ primarily from plants of 'USCAL91001' in flower color as plants of 'USCAL91001' have red purple-colored flowers with yellow-colored stripes that extend to the edge of the petal.

Plants of the new *Calibrachoa* can also be compared to plants of the *Calibrachoa* sp. 'USCAL42202', disclosed in U.S. Plant Pat. No. 27,008. In side-by-side comparisons, plants of the new *Calibrachoa* differ primarily from plants of 'USCAL42202' in flower color as plants of 'USCAL42202' have violet-colored flowers with purple-colored stripes.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'USCAL69404' grown in a container.

The photograph at the top of the sheet is a close-up view of a typical flowering plant of 'USCAL69404'.

DETAILED BOTANICAL DESCRIPTION

The aforementioned photographs and following observations and measurements describe plants grown during the spring in 11.5-cm containers in an acrylic-covered greenhouse in Carleton, Mich. and under cultural practices typical of commercial *Calibrachoa* production. During the production of the plants, day and night temperatures ranged from 18° C. to 27° C. Plants were six weeks from planting rooted cuttings when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCAL69404'.

Parentage:

*Female, or seed, parent*.—Proprietary selection of *Calibrachoa* sp. identified as code number 14CJ21-01, not patented.

*Male, or pollen, parent*.—Proprietary selection of *Calibrachoa* sp. identified as code number 14CJ26-02, not patented.

Propagation:

*Type*.—By vegetative terminal cuttings.

*Time to initiate roots, summer*.—About five to seven days at temperatures ranging from 17° C. to 29° C.

*Time to initiate roots, winter*.—About seven to ten days at temperatures ranging from 17° C. to 21° C.

*Time to produce a rooted plant, summer*.—About four to five weeks at temperatures ranging from 17° C. to 29° C.

*Time to produce a rooted plant, winter*.—About five to six weeks at temperatures ranging from 17° C. to 21° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Upright to outwardly spreading and mounding to eventually trailing plant habit; moderately vigorous to vigorous growth habit; moderate growth rate; freely branching habit with about five primary lateral branches each with about three secondary branches; dense and bushy appearance.

*Plant height, soil level to top of foliar plane*.—About 10.5 cm.

*Plant height, soil level to top of floral plane*.—About 13 cm.

*Plant diameter*.—About 28 cm.

Lateral branch description:

*Length*.—About 13 cm to 14 cm.

*Diameter*.—About 1.5 mm.

*Internode length*.—About 1.8 cm.

*Strength*.—Strong.

*Aspect*.—Initially upright then outwardly spreading to eventually trailing.

*Texture and luster*.—Minute pubescence; matte.

*Color, developing*.—Close to 144A.

*Color, developed*.—Close to 146B.

Leaf description:

*Arrangement*.—Before flowering, alternate; after flowering, opposite; leaves simple.

*Length*.—About 2.6 cm.

*Width*.—About 1 cm.

*Shape*.—Elliptical.

*Apex*.—Rounded to broadly acute.

*Base*.—Attenuate.

*Margin*.—Entire.

*Texture and luster, upper and lower surfaces*.—Minute pubescence; matte.

*Venation pattern*.—Pinnate; arcuate.

*Color*.—Developing leaves, upper surface: Close to 146A. Developing leaves, lower surface: Close to 146B. Fully expanded leaves, upper surface: Close to N137B; venation, close to 146B. Fully expanded leaves, lower surface: Close to 147B; venation, close to 147C.

*Petioles*.—Length: About 6 mm. Diameter: About 2 mm. Strength: Moderately strong. Texture and luster, upper and lower surfaces: Mostly smooth with scattered pubescence; matte. Color, upper and lower surfaces: Close to 146C.

Flower description:

*Flower type and flowering habit*.—Single salverform flowers arising from leaf axils; freely flowering habit with typically about 270 flowers and flower buds developing per plant; flowers face upright to outwardly.

*Fragrance*.—None detected.

*Natural flowering season*.—Plants of the new *Calibrachoa* begin flowering about six weeks after planting; plants flower continuously from the spring though the summer until frost.

*Flower longevity*.—Individual flowers last about four to five days on the plant; flowers persistent.

*Flower buds*.—Length: About 2.2 cm. Diameter: About 5 mm. Shape: Oblong, elongate. Texture and luster: Minute pubescence; matte. Color: Close to 152B to 152C.

*Flower diameter*.—About 2.6 cm by 2.4 cm.

*Flower length (height)*.—About 2.4 cm.

*Flower throat diameter*.—About 4 mm by 7 mm.

*Flower tube length*.—About 1.8 cm.

*Flower tube diameter*.—About 4 mm.

*Corolla*.—Arrangement: Five fused petals opening into a flared trumpet; lobes recurved. Petal lobe length (from throat): About 1.2 cm. Petal lobe width: About 1.5 cm. Petal shape: Fan-shaped. Petal apex: Rounded. Petal margin: Entire. Petal texture and luster, upper surface: Smooth, glabrous, velvety; matte. Petal texture and luster, lower surface: Minute pubescence especially along the veins; matte. Throat texture and luster: Smooth, glabrous; slightly glossy. Tube texture and luster: Minute pubescence; matte. Color: Petal lobe, when opening, upper surface: Close to 187B to 187C. Petal lobe, when opening, lower surface: Close to more grey than N170D. Petal lobe, fully opened, upper surface: Ground color, close to 53A; band surrounding the throat, darker red than 53A; narrow radiating stripes, close to 12A; venation, close to 53A; with development, ground color becoming closer to 53B and band, closer to 53A. Petal lobe, fully opened, lower surface: Close to 186C; narrow radiating stripes, close to 2C; venation, close to 187B to 187C; color does not fade with development. Throat: Close to 16A; venation, close to 153C. Tube: Close to slightly more grey than 153D; venation, close to 183B.

*Calyx*.—Arrangement: One star-shaped calyx tube with five sepals fused towards the base and arranged in a single whorl. Length: About 1.2 cm. Diameter: About 8 mm. Sepal length: About 6 mm. Sepal width: About 2 mm. Sepal shape: Lanceolate. Sepal apex: Acute. Sepal margin: Entire. Sepal texture and luster, upper and lower surfaces: Minute pubescence; matte. Sepal color, upper and lower surfaces: Close to 146A.

*Peduncles*.—Length: About 1.8 cm. Diameter: About 1 mm. Angle: About 30° to 45° from stem axis. Strength: Moderately strong. Texture and luster: Minute pubescence; matte. Color: Close to 146B.

*Reproductive organs*.—Stamens: Quantity: Four per flower. Filament length: About 1.2 cm. Filament color: Close to 145B. Anther size: About 1 mm by 1 mm. Anther shape: Round. Anther color: Close to 3B. Pollen amount: Moderate. Pollen color: Close to 9C. Pistils: Quantity: One per flower. Pistil length: About 1.9 cm. Style length: About 9 mm. Style color: Close to 145C. Stigma diameter: About 1 mm. Stigma shape: Oval. Stigma color: Close to 146B. Ovary color: Close to 146D. Seeds and fruits: Seed and fruit development have not been observed on plants of the new *Calibrachoa* to date.

Garden performance: Plants of the new *Calibrachoa* have been observed to have good garden performance and tolerate wind, rain and to be suitable for USDA Hardiness Zones 9 to 11.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'USCAL69404' as illustrated and described.

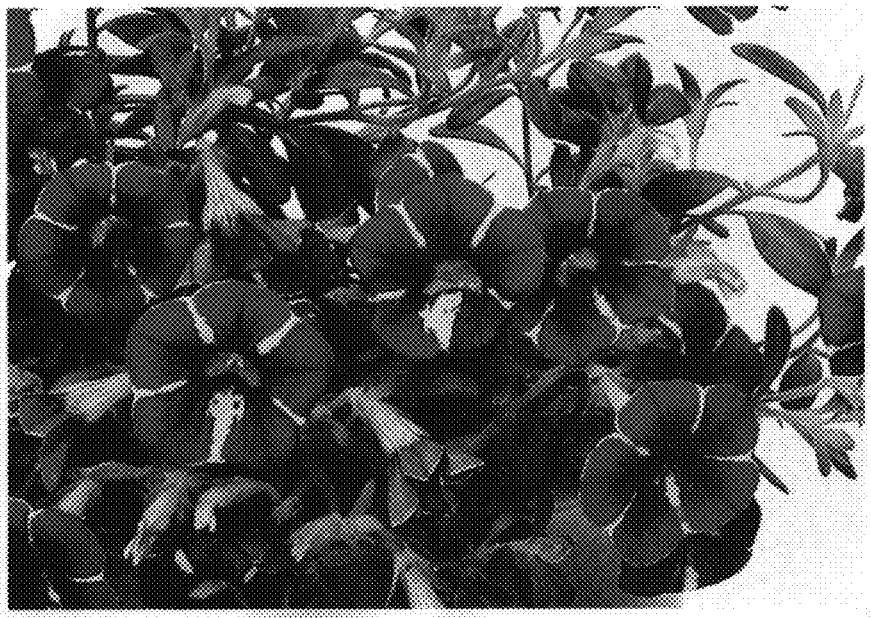
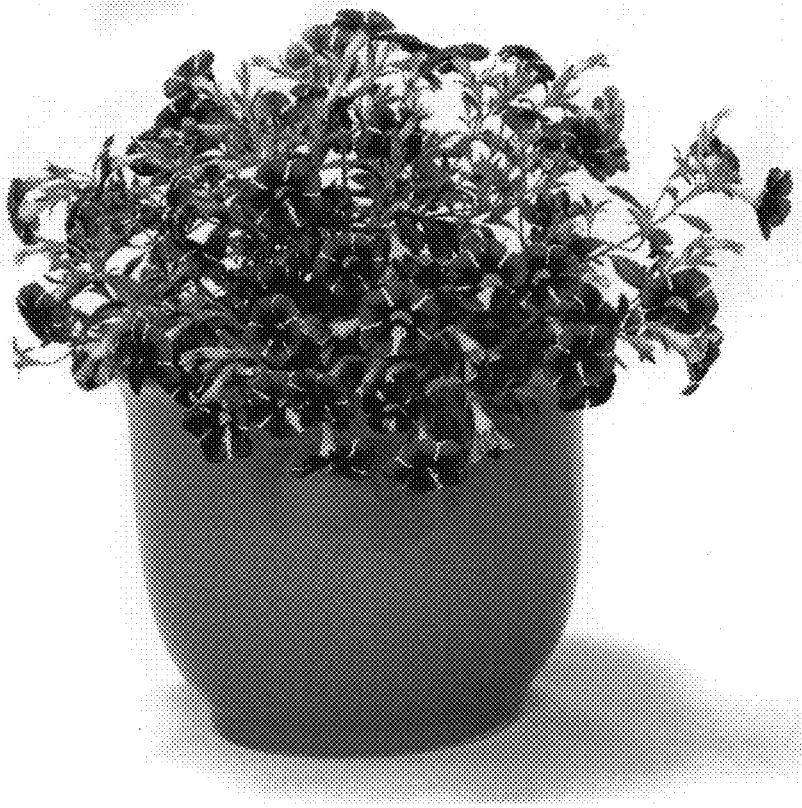

* * * * *